United States Patent
Didier

(10) Patent No.: US 9,956,117 B2
(45) Date of Patent: May 1, 2018

(54) FACE FIT ADJUSTMENT SYSTEM

(75) Inventor: Bertrand Didier, Granges-Paccot (CH)

(73) Assignee: Scott Sports SA, Givisiez (CH)

( * ) Notice: Subject to any disclaimer, the term of this patent is extended or adjusted under 35 U.S.C. 154(b) by 1561 days.

(21) Appl. No.: 13/516,827

(22) PCT Filed: Jan. 8, 2010

(86) PCT No.: PCT/EP2010/000065
§ 371 (c)(1),
(2), (4) Date: Jun. 18, 2012

(87) PCT Pub. No.: WO2011/082718
PCT Pub. Date: Jul. 14, 2011

(65) Prior Publication Data
US 2012/0255104 A1    Oct. 11, 2012

(51) Int. Cl.
| | | |
|---|---|---|
| *A61M 16/06* | (2006.01) | |
| *A61F 9/02* | (2006.01) | |
| *A62B 18/08* | (2006.01) | |

(52) U.S. Cl.
CPC ............. *A61F 9/026* (2013.01); *A61F 9/025* (2013.01); *A61M 16/0605* (2014.02); *A61M 16/06* (2013.01); *A62B 18/082* (2013.01)

(58) Field of Classification Search
CPC ............. A61F 9/02; A61F 9/027; G02C 1/00

USPC .................................................. 2/426; 9/426
See application file for complete search history.

(56) References Cited

U.S. PATENT DOCUMENTS

| | | | | |
|---|---|---|---|---|
| 2,582,554 A | * | 1/1952 | Mendelsohn | 351/48 |
| 2,618,782 A | * | 11/1952 | Christensen et al. | 2/436 |
| 5,191,364 A | * | 3/1993 | Kopfer | A61F 9/02 |
| | | | | 2/436 |
| 5,469,229 A | * | 11/1995 | Greenbaum | 351/44 |
| 5,802,622 A | * | 9/1998 | Baharad et al. | 2/434 |
| 6,732,382 B2 | * | 5/2004 | Dondero | 2/436 |
| 8,800,066 B2 | * | 8/2014 | Hooper et al. | 2/435 |
| 2004/0148684 A1 | * | 8/2004 | Wiedner | 2/428 |
| 2005/0015862 A1 | * | 1/2005 | Dondero | 2/436 |
| 2009/0165184 A1 | * | 7/2009 | Hogen | 2/15 |

FOREIGN PATENT DOCUMENTS

DE            20109028 U1    8/2001

* cited by examiner

*Primary Examiner* — Richale Quinn
(74) *Attorney, Agent, or Firm* — patenttm.us

(57) ABSTRACT

The invention relates to a face cover device providing a closure over a predetermined area of a face, having a functional part (2) and a face rest part (1) which are interconnected by one connecting section or a plurality of connecting sections (3, 8), characterized in that the one connecting section or at least one of the plurality of connecting sections is an adjustable connecting section (3) that allows for adjusting the position of the face rest part relative to the functional part.

23 Claims, 6 Drawing Sheets

SECTION 1 1

SECTION 1-1

SECTION 1-1

SECTION 1-1

FIG 9
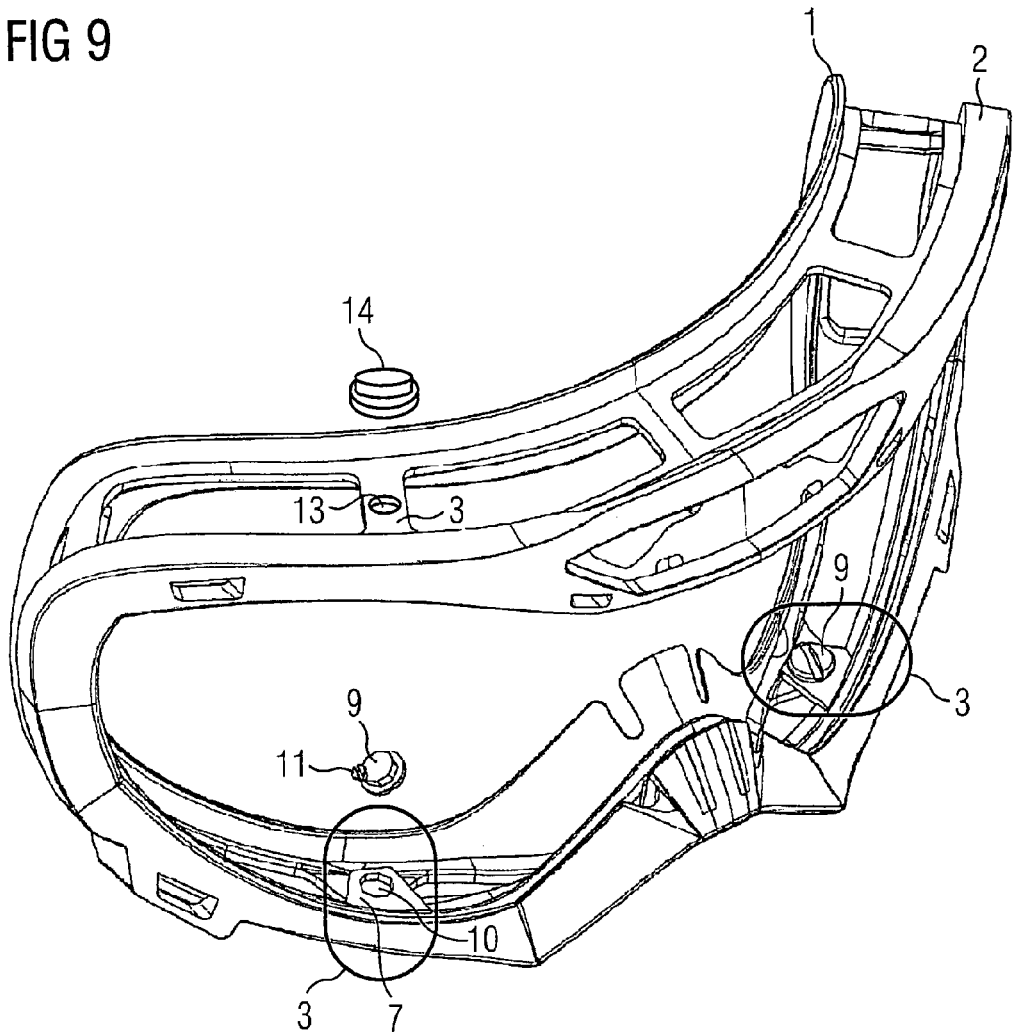
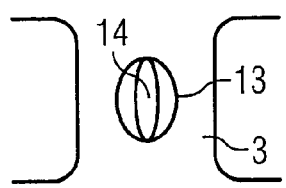
FIG 10a
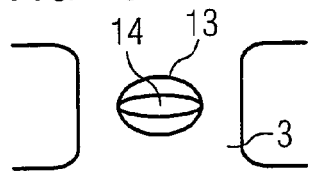
FIG 10b
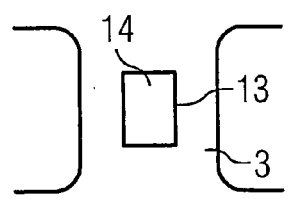
FIG 10c
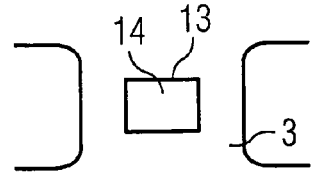
FIG 10d

FACE FIT ADJUSTMENT SYSTEM

The present invention relates to a face cover device such as goggles or a face mask that provides an improved fit to a user's face.

Face cover devices providing a closure over a predetermined area of a human face are widely used for a variety of purposes. Such face cover devices might be goggles such as sport goggles for various kinds of sports such as biking, motorcycling, diving, sky-diving, paintball, snowmobiling, quading, snow sport, etc., army goggles, protective goggles for fire fighters, policemen, machinists, mechanics, etc., safety goggles, e.g. for industrial use, for use in laboratories such as physical, chemical or biological laboratories, and all kinds of safety goggles for eye protection. Such face cover devices might also be face masks such as breathing masks for industrial or medical use or air or oxygen masks for fire fighters, pilots, etc.

For such face cover devices to perform the intended function, a close fit to the user's face is usually important. The close fit is desired in a sealing area, surrounding the area over which a closure is to be formed, such that a certain sealing of the closure according to the purpose of the face cover device is obtained. Further, in order to provide wearing comfort and to prevent undesired pressure points, a uniform pressure should be exerted by the face cover device on the user's face especially in the sealing area.

However, every user has a different face shape, in particular temples, cheek area, forehead, nose, chin, etc., so that a face cover device having a given specific shape cannot fit every user in the same manner and provide the same wearing comfort. A slight misfit will result in an unintentionally distributed pressure in the sealing area, e.g. a non-uniform pressure, exerted by the face cover device on the human face. This will reduce the wearing comfort and possibly cause pressure points on a user's face. A greater misfit will result in insufficient sealing in the sealing area, whereby the intended function of the face cover device might be impaired. For example, dust might enter the closure provided by motorcycle goggles, or water might enter the closure of a diving mask.

Usually, diving masks provide a closure around the eyes and the nose. They comprise a glass plate in front of the eyes and a skirt of rubber or silicone to create a watertight seal with the diver's face, while a belt or strap around the diver's head keeps the diving mask in position on the diver's face. The skirt ends on the surface of the user's face in order to provide a sufficiently strong watertight seal. The set-up of breathing masks and air masks, which provide a closure over the nose and the mouth of the user, is regarding the sealing similar. The force exerted by the strap can be adjusted in order to select the best possible pressure of the diving mask on the diver's face. This permits slight misfits between the shape of the diver's face and the shape of the face for which the diving mask is designed to be overcome. However, if the misfit is too great, there will be pressure points on the diver's face where the diving mask exerts an elevated pressure, and a reliable function of the diving mask will also be jeopardized.

In other types of face cover devices such as snow sport goggles, which involve lower requirements for the sealing of the closure, the seal is provided by a first frame lying tight against the surface of a human face. The first frame is frequently a closed frame. A second frame, arranged perpendicular, i.e. substantially normal to the surface of the human face, above the first frame, carries a transparent windshield. The first and the second frame are connected by one or several connecting sections and the two frames might be made of a single piece. On the lateral surface surrounding the first and second frames of the snow sport goggles, where the connecting sections are located, gaps might be provided which are covered by e.g. a breathable material in order to provide sufficient air tightness and a sufficient ventilation of the goggles at the same time. In sum, the two frames provide a framework for closure over the area of the eyes of a user's face. Such goggles, especially the frames thereof, are frequently flexible such that the force exerted by the strap by which the goggles are fixed to the user's head can slightly deform the goggles in order to adapt the shape of the goggles to the shape of the user's face and to overcome a possible misfit. Additionally, it is known to provide a foam layer beneath the first frame in order to seal the closure over the user's face and to reduce gaps and pressure points in the sealing area of the user's face. Improved approaches provide such a foam layer with varying thicknesses, densities or shapes in the sealing area beneath the first frame.

However, even with such approaches the results remain unsatisfactory and there is still a desire to improve the fit, and ensure the function, of such goggles.

Accordingly, it is an object of the present invention to provide a face cover device providing reliable function and improved wearing comfort for different face shapes.

The object is solved by a face cover device according to the independent claim. The dependent claims define preferred arrangements.

The inventive face cover device relates to face masks, goggles, etc., that provide a closure over a predetermined area of a user's face, i.e. of a human face. Such a face cover device is preferably fixed to the user's head by means of a belt or strap, such as a retaining strap, preferably made of an elastic, rubber-like material. The closure is a closed space sealed from the outside of the face cover device, whereby the extent, nature and strength of the seal are adapted to the intended purpose of the face cover device.

The face cover device comprises a functional part that provides the desired functions of the face cover device comprising e.g. a transparent layer for wind-shielding or a tube inlet section for providing breathable air for breathing or air masks. The functional part possibly further comprises a closure part such as an elastic skirt or breathable material for completing the closure over the predetermined area of the user's face. The closure part might be located on the lateral surface of the face cover device above the sealing area of the user's face.

The inventive face cover device further comprises a face rest part that preferably has a flat surface lying tight against the surface of a user's face. The face rest part is adapted to the shape of the human face in an area surrounding the predetermined area of the face over which a closure is to be formed in order to provide a tight fit of the face cover device on a user's face.

The face rest part and the functional part are mechanically interconnected by one or a plurality of connecting sections.

According to the invention the one connecting section or at least one of the plurality of connecting sections is constituted as an adjustable connecting section. Such an adjustable connecting section allows for adjusting the position of the face rest part relative to the functional part. The adjustable connecting section allows preferably for adjusting the distance between the face rest part and the functional part in a direction normal to the surface of the user's face and/or for adjusting the lateral position of the face rest part relative to the functional part in a direction parallel to the surface of the user's face. The position of the face rest part and the functional part relative to each other is preferably adjusted by selecting one of a plurality of predetermined positions of the adjustable connecting section, where each of the plurality of predetermined positions of the adjustable connecting section defines a relative arrangement of the face rest part and the functional part.

This adjustment allows for positioning the functional part of the face cover device over the user's face such that the intended function of the face cover device can be advantageously provided. In the case of goggles, this allows for example for selecting a suitable distance of the transparent part of the functional part from the eyes of a user. This is especially advantageous in case the transparent layer has a lens function. In case protruding parts of the user's face such as the nose or the chin are to be covered by the face cover device, as is the case with breathing or air masks, the adjustment provided by the adjustable connecting section assures that such protruding parts are safely included in the closure formed by the face cover device. This adjustment also allows for positioning the face rest part of the face cover device on the user's face, such that a close fit is obtained.

As described above, many face cover devices such as diving goggles are comprised of a rigid part, such as a glass plate, and a closure part, such as a skirt of a rubber-like, flexible material, surrounding it to provide a seal. Breathing or air masks provide a similar set-up regarding the sealing, whereby instead of a glass plate a tube entry for breathable air is provided.

In order to provide a sufficiently strong seal to cope with an elevated pressure difference between the inside of the face cover device, i.e. the closure created thereby, and the outside of the face cover device, the skirt frequently terminates directly on the surface of the human face. The inventive face rest part, in combination with the at least one adjustable connecting section that is preferably connected to a rigid part of the functional part, provides for adjusting the pressure of the skirt exerted on the surface of the human face. Therefore, the optimum pressure of the skirt on the human face can be selected such that best results such as an optimum seal are obtained.

The retaining strap can be attached to the face rest part or preferably to the functional part.

In a preferred arrangement of the face cover device, a plurality of adjustable connecting sections are provided, which each allow for adjusting the position of the face rest part relative to the functional part independently of each other, in particular the positions of the sections of the functional part and the face rest part where the plural adjustable connecting sections are arranged. The plural adjustable connecting sections are preferably provided as distinct parts. The provision of plural adjustable connecting sections that can be adjusted independently of each other allows for providing connecting sections that are set up in a simple manner, while the functional part can be positioned relative to the face rest part in various selectable ways. For example, an inclination of the functional part relative to the face rest part and, thus, relative to the face of the user can be provided by providing a plurality of adjustable connecting sections each allowing for adjusting only the distance between the face rest part and the functional part.

In a further preferred embodiment, the face rest part of the face cover device is comprised of a plurality of sections which are mechanically independent of each other. The plurality of sections are preferably arranged to surround the predetermined area of the user's face over which the face cover device is to provide a closure. Each of the plurality of sections is connected to the functional part by at least one adjustable connecting section, whereby each of the adjustable connecting sections allows for an independent adjustment of the position of the respective section of the face rest part relative to the functional part of the face cover device. When the functional part has a rigid part such as the glass plate of goggles, this allows for an adaptation of the face rest part to the shape of a user's face by individually adjusting the position of the plural sections of the face rest part relative to the functional part of the face cover device by means of the adjustable connecting sections which can be adjusted independently of each other. This allows the same pressure to be exerted by each of the plural sections and, thus, for a uniform pressure to be exerted by the face cover device on a user's face. The adjustable connecting sections preferably interconnect the plural sections of the face rest part with a rigid part of the functional part.

In a further preferred arrangement, the face rest part is provided as a flexible element, e.g. made of a flexible material. If the face rest part is divided into plural sections, several or each of the sections might be made of such a flexible material. In a preferred alternative arrangement, however, the face rest part is provided as a closed frame surrounding or being part of the predetermined area of the face over which the face cover device is to provide a closure. In a particularly preferred embodiment, the face rest part is flexible and provided as a single piece completely surrounding the predetermined area of the user's face. When the face rest part is flexible, the same advantages as described above for the case of the face rest part being comprised of plural sections can be obtained even when the face rest part is provided as a single piece, such as a closed frame. In other words, by the provision of the closed frame as a flexible element which is connected to the functional part of the face cover device by a plurality of adjustable connecting sections each allowing for independently adjusting the position of the face rest part in sections where an adjustable connecting section is provided relative to the functional part independently of each other, the face rest part can be adapted to the individual shape of a user's face. A close contact and a good fit of the face rest part with the user's face can thereby be assured, while a uniform pressure on each part of the face rest part can be provided. Preferably, the face rest part has a flat surface lying against the surface of a user's face. On the one hand, this allows for avoiding pressure points on the user's face and, thus, for improving the wearing comfort. On the other hand, it allows for an improved seal by the face rest part on the user's face. In case the improved seal provided by the face rest part is sufficient for the seal to be provided by the face cover device, a closure part of the functional part, which preferably surrounds the functional part completely, such as a skirt of a diving mask, does not need to terminate directly on the skin of the face any more. The closure part might rather terminate directly on the face rest part, which simplifies the construction of the face cover device. The improved seal of the face rest part is advantageous for the intended function of the face cover device of providing a closure over a predetermined area of a user's face. In this case, a closure part of the functional layer of the face cover device has to be capable of coping with the various positions of the face rest part relative to the functional part that might be adjusted by means of the plurality of adjustable connecting sections.

This can be achieved by using an elastic or rubber-like material e.g. a plastic for the closure part of the functional part, allowing for a sufficient deformation while maintaining the intended closure functionality, by providing the closure part in a pre-deformed shape, such as a wavy shape, which allows an easy deformation of the closure part. Alternatively or additionally the closure part may be provided as two overlapping layers that are allowed e.g. to slide on or into each other when the positions of the face rest part and the functional layer are adjusted relative to each other by means of the adjustable connecting sections. On that purpose the two overlapping layers might be constituted as corresponding male and female parts. According to the purpose of the face cover device, the closure part might be made of breathable material, such as woven textile, fabric, or a membrane, of non-breathable material or of foam. The functionality of the closure part might also be provided by the functional part or portions thereof such as a frame of the functional part. On that purpose the functional part or the portions thereof might be flexible in order to provide a easy deformation, while maintaining a sufficient seal of the closure of the face cover device.

In a further preferred arrangement, the functional part and the face rest part are arranged as a single piece. Thus, in addition to the at least one adjustable connecting section, at least one additional connecting section is provided between the face rest part and the functional part of the face cover device that is not adjustable and provides for a fixed position of at least parts of the face rest part relative to the functional part. The provision of such fixed, additional connecting sections increases the mechanical stability of the face cover device, but limits the possibilities to adjust the face rest part relative to the functional part as a whole. Such an arrangement is thus preferable when only a limited adaptation of the face cover device is necessary or desired. In this arrangement, the adjustable connecting sections are preferably provided on those parts of a face cover device where the greatest variations between the shapes of different users' faces are to be expected.

In a further preferred arrangement, each connecting section is releasable, regardless of whether a given connecting section is an adjustable connecting section or a connecting section that does not provide for a selection of different positions and rather provides only one position. The releasing part of an adjustable connecting section is preferably different from the part of the adjustable connecting section allowing for the intended adjustment. When the face rest part and the functional part are connected exclusively by releasable connecting sections, the face rest part and the functional part constitute two distinct elements that can be separated from each other. This allows for providing either the face rest part or the functional part as an exchangeable element. In case the functional part is the exchangeable element, a given user can use the same face rest part in combination with one of a plurality of different functional parts. This allows for using a face rest part that is perfectly adjusted to the shape of the face of a given user in combination with a plurality of face cover devices. In a preferred embodiment, the face rest part constitutes the exchangeable element. This allows for selecting one of a plurality of face rest parts for a given face cover device. This selection of a face rest part preferably allows for providing at least a rough adjustment of the face cover device to the face shape of a given user, while the at least one adjustable connecting section preferably allows for a fine adjustment. The releasing part of the adjustable or non-adjustable connecting sections might be provided as mechanical releasable parts, as magnetically releasable parts, as a Velcro strip, etc.

Correspondingly, the present invention also relates to a system comprising the above-described preferred arrangement of a face cover device, comprising a face rest part and functional part, and an additional further face rest part that is capable of being exchanged with the first face rest part of the face cover device.

An adjustable connecting section can be set up in various different ways.

In a preferred embodiment the adjustable connecting section comprises an adjustable part constituted as single piece. The shape especially the length of the adjustable part can be selectably changed, i.e. the adjustable part can be deformed, e.g. retracted or elongated, such that the relative position of the face rest part and the functional part of the face cover device can be suitably selected. The adjustable part might be fixedly attached to the face rest part and/or the functional part of the face cover device directly or via additional parts. In an especially preferred embodiment, the deformable part and the face rest part and/or the functional part are constituted as a single piece.

In a preferred embodiment, the adjustable part is plastically deformable, i.e. the shape thereof can be adjusted, upon influence of an external influence such as heat, electric or magnetic fields or electric power. The adjustable part is rigid, i.e. at most slightly elastically deformable, in the absence of such an external influence. Thus, with such an external influence present, the shape of the adjustable part can be chosen such that the face rest part and the functional part are suitably positioned relative to each other, while in the absence of the external influence the deformable part maintains the selected shape and is rigid apart from e.g. a minor elastic deformation that might occur upon action of external forces. Such an adjustable part might be made of a duroplastic or thermoplastic material allowing for adjusting the shape of the connecting section one-time or a plurality of times, respectively, when applying heat.

In an alternative embodiment, the adjustable part is made of a flexible material, i.e. the adjustable part is elastically deformable independent of e.g. the presence of an external influence. The adjustable part comprises a hole, preferably a through hole, and the adjustable part is arranged such that the whole adjustable part changes its shape when the hole is deformed. Thus, upon deformation of the hole of the adjustable part, the adjustable connecting section is adjusted, and the face rest part is positioned relative to the functional part of the face cover device. The hole is preferably deformed upon insertion of an inserting member in the hole. In case only a part of the inserting member is to be inserted into the hole, in the following the term "inserting member" relates to that part of the inserting member, while the remaining part of the inserting member might be shaped suitable, e.g. in order to provide easy operation. The shape of the inserting member deviates from the shape of the hole in the relaxed state of the adjustable part, such that the hole is purposively deformed when the inserting member in inserted into the hole. The inserting member is less flexible, i.e. more rigid than the adjustable part. Further the shape of the hole and the inserting member are adapted to each other such that the deformation of the hole, and thus the deformation of the adjustable part, depends on the angular position of the inserting member within the hole. This might be achieved by arranging the inserting member such that a first dimension thereof taken along a first direction across to the hole is larger than a second dimension thereof taken along a second direction across to the hole, where the second direction is different from, preferably perpendicular to the first direction. Preferably the circumferential lengths of the hole in its relaxed state and the inserting member, i.e. the part of the inserting member with is to be inserted into the hole, are at least substantially identical.

For example the hole might be circularly shaped in its relaxed state, while the inserting member is non-circularly, e.g. elliptically or oval shaped. The first dimension of the inserting member is larger than the diameter of the hole in its relaxed state, while the second dimension is smaller that the diameter of the hole. In the case of an elliptically shaped inserting member, the long axis of the underlying ellipse constitutes the first dimension, while the short axis thereof constitutes the second dimension. When the inserting member is inserted into the hole, the hole equally takes an elliptical form, resulting in an elongation of the adjustable part in the direction of the long axis of the elliptically shaped inserting member. Thus, when the long axis is oriented such that it points to the face rest part and the functional part, the adjustable part of the adjustable connecting section becomes longer and thinner, i.e. the face rest part and functional part are moved away from each other, when compared with the relaxed state of the adjustable part. In contrast, when the short axis is oriented such that it points to the face rest part and the functional part, the adjustable part of the adjustable connecting section becomes shorter and thicker, i.e. the face rest part and functional part are approached to each other, when compared with the relaxed state of the adjustable part.

In an alternative example, the hole has a square shape in its relaxed state and the inserting member has a rectangular shape, where the underlying rectangle has a short and a long side. Upon insertion of the inserting member into the hole, the hole adopts the rectangular shape at least partly, which leads to the adjustable part becoming longer and thinner or shorter and thicker, and correspondingly the face rest part and the functional part being moved away from each other or approached to each other, respectively, depending on the orientation of the rectangular inserting member within the hole.

Similar effects on the dimension of the adjustable part can be achieved when the hole and the inserting member have other shapes such as triangular, pentagonal, hexagonal or octagonal shapes. While in the two previously described configurations the face rest part and the functional part are arranged maximally and minimally distant from each upon turning of the inserting member by 90°, in the later configurations, this angle might be smaller, e.g. 60° in the case of a equilateral triangles and 30° in the case of regular hexagons.

In a further preferred embodiment, the adjustable connecting section is constituted of a plurality of pieces. It comprises a first part that is fixed to the face rest part and a second part that is fixed to the functional part. The first part can be fixedly attached to the face rest part, or the first part and the face rest part can be provided as a single piece. Equivalently, the second part can be fixedly attached to the functional part, or the second part and the functional part can by provided as a single piece. The first and the second part and, thus, the sections of the face rest part and the functional part where the first and second parts are located, can be selectably positioned relative to each other such that the face rest part and the functional part adopt one of a plurality of different positions relative to each other. In other words, the adjustable connecting section allows for selecting a position of the functional part relative to the face rest part, the position being preferably predetermined. The selection of the various positions might be based on mechanical interaction of two or more parts, on magnetic and/or electric forces, on a Velcro stripe or similar systems capable of exerting mechanical forces. The adjustable connection section having a first and a second part might be additionally provided with an adjustable part as described above in order to provide an increased degree of adjustment of the face rest part relative to the functional part.

In a preferred embodiment, the adjustment of the first part relative to the second part is achieved by providing a single pin on the first part and several corresponding holes on the second part, or vice versa, such that the pin can selectably engage one of the several holes. Accordingly, the face rest part and the functional part adopt different positions relative to each other. Alternatively, several pins are provided on one of the first and the second part, while a single hole is provided on the other one of the first and the second part. In an especially preferred arrangement, several pins are provided on one of the first and the second part and several holes are provided on the other one of the first and the second part, which allows for a large number of different positions that can be selected. While the pins and the holes are oriented along a common axis, this common axis is preferably oriented such that the force that will be exerted on the face cover device, e.g. upon fixing of the face cover device on the user's face or during use of the face cover device, does not act along a common axis. Preferably, the pin engages a corresponding hole frictionally, which can be easily realized when the material from which the pins are formed and in which the holes are formed is a flexible material, such as plastic or rubber, especially a molded plastic. Preferably, the pins and holes are arranged such that the intended adjustment, e.g. a variation of the distance between the face rest part and the functional part, can be carried out.

In a variant of this embodiment, first and second magnets are provided on the first and second parts, respectively, instead of or in addition to the pins and holes. The first and second magnets are oriented relative to each other such that an attractive force acts between them, allowing for a selection of one of several distinct predetermined positions of the first part relative to the second part.

In an alternative arrangement, one of the first and the second part is constituted of or comprises a slider and the other one of the first and the second part is constituted of or comprises a slot which the slider can engage at selectably different positions. This permits an adjustment to be carried out in a direction in which the slider and the slot engage. The external surfaces of the slider and the internal surfaces of the slot can be plane, allowing for a frictional engagement of the slider within the slot and, thus, for a continuous selection of different positions. Alternatively, one or several external surfaces of the slider can be provided e.g. in a wavy manner such that protrusions arise, and one or several corresponding internal surfaces of the slot with corresponding recesses, allowing for a form fit engagement of the slider within the slot and, thus, for a selection of one of several distinct predetermined positions of the slider within the slot. Preferably, two opposing surfaces of each of the slot and the slider are provided with such protrusions and recesses.

In a variant of this embodiment, first and second magnets are provided on the slot and the slider, respectively, instead of or in addition to the protrusions and recesses. The first and second magnets are oriented relative to each other such that an attractive force acts between them, allowing for a selection of one of several distinct predetermined positions of the slider within the slot.

In a further preferred arrangement of the adjustable connecting section of the face cover device, an additional connecting member is provided, which connects the first and the second part. For this purpose, the connecting member can be fixed to the first and the second part in a plurality of selectably different manners, each providing a different positioning of the first part relative to the second part and thus of the face rest part relative to the functional part.

In a further preferred arrangement, the connecting member is inserted into a hole in one of the first and the second part at one of a plurality of selectably different angular positions. The connecting member and the hole have corresponding shapes, such as a circular shape, allowing for a frictional engagement of the connecting member in the hole with respect to different angular positions and for a continuous selection of different angular positions. Alternatively, the connecting member and the hole might be rectangular, elliptical, triangular, square, hexagonal, octahedral, etc., allowing for a form fit engagement of the connecting member in the hole with respect to different angular positions and a corresponding distinct selection of two, three, four, six, eight, etc., different angular positions of the connecting member within the hole. The connecting member further comprises at least one pin, which is arranged eccentrically on the connecting member, and the other one of the first and second parts comprises a hole, which the eccentrically arranged pin can engage. Alternatively, the position of the pin and the hole can be exchanged.

In an alternative arrangement, an arranging member provides for connecting the first and the second part of the connecting section in exactly one position relative to each other. In this arrangement, the arranging member is provided as an exchangeable part, whereby different exchangeable arranging members provide for different positions of the first part relative to the second part. Accordingly, the invention also pertains to a system comprising a face cover device and a plurality of arranging members, where each of the arranging members connects and arranges the first and the second part in exactly one position in each case, while different arranging members define different positions of the first and the second part relative to each other. The use of one of a plurality of arranging members as exchangeable parts which each define exactly one position of the first and the second part of the connecting section allows for avoiding an inadvertent change in a previously selected position.

The adjustment mechanism of an adjustable connecting section might be realized by any suitable adjustment system. For example, for adjusting the fit of a helmet, such as a bike helmet, to a user's head, the helmet is disposed above the head of a driver by means of an adjustable support system. The circumferential length of the support system can be adjusted by turning a toothed wheel, the tooth of which engage with corresponding tooth arranged on the support system, such that two end portions of the support system are moved relative to each other leading to a shortening and lengthening of the circumferential length of the support system in dependence of the direction of rotation of the toothed wheel. Such a system might be miniaturized and adapted for use within the at least one adjustable connecting section of the face cover device.

The various arrangements of the connecting section can be combined with each other. For example, a connecting member might be provided as an exchangeable part, in order to increase the degree of adjustment available for a connecting section. Alternatively, plural adjustment mechanisms might be provided in a single adjustable connecting section. Further a face cover device might be provided with a plurality of connecting sections, which are based on different adjustment mechanisms, i.e. plural connecting sections set up in different manners might be arranged on a given face cover device. This makes it possible to provide on each part of the face cover device the adjustable connecting section best suited for a given purpose, such as the provision of an easy adjustment by the user as well as the prevention of an inadvertent change of the selected position.

The various arrangements of the adjustable connection section described above have been substantially based on frictional and/or form fit engagement of plural corresponding mechanical parts such as pins and holes, possibly provided with protrusions and corresponding recesses. Similar modes of operation can be obtained when alternatively or additionally other systems, which provide suitable mechanical forces, are provided, such as magnetic systems, Velcro stripes or systems based on electric forces. For example, instead of a pin and a corresponding hole, a pair of suitably oriented magnets might be provided, that provide suitable attractive forces. In case plural, preferably identical pairs of magnets are suitably arranged plural predetermined distinct positions might be selected. Equally, such pairs of magnets might be provided instead of or in addition to protrusions and corresponding recesses. Velcro stripes provide similar degrees of freedom to select the relative arrangement of two mechanical parts within an adjustable connecting section. The present invention extends to adjustable connecting sections, the adjustment mechanism being based on magnetic and/or electric forces, Velcro stripes, and similar systems.

Further embodiments and advantages of the invention will be exemplified by means of the accompanying figures. The illustrated examples constitute preferred embodiments which do not limit the invention. The figures are schematic drawings that do not represent the real dimensions, but are intended for providing a good understanding of the various embodiments.

FIG. 9 shows a perspective view of a fourth embodiment of goggles; and

FIGS. 10a to 10d show plan views of arrangements of an adjustable parts.

Figure 1:
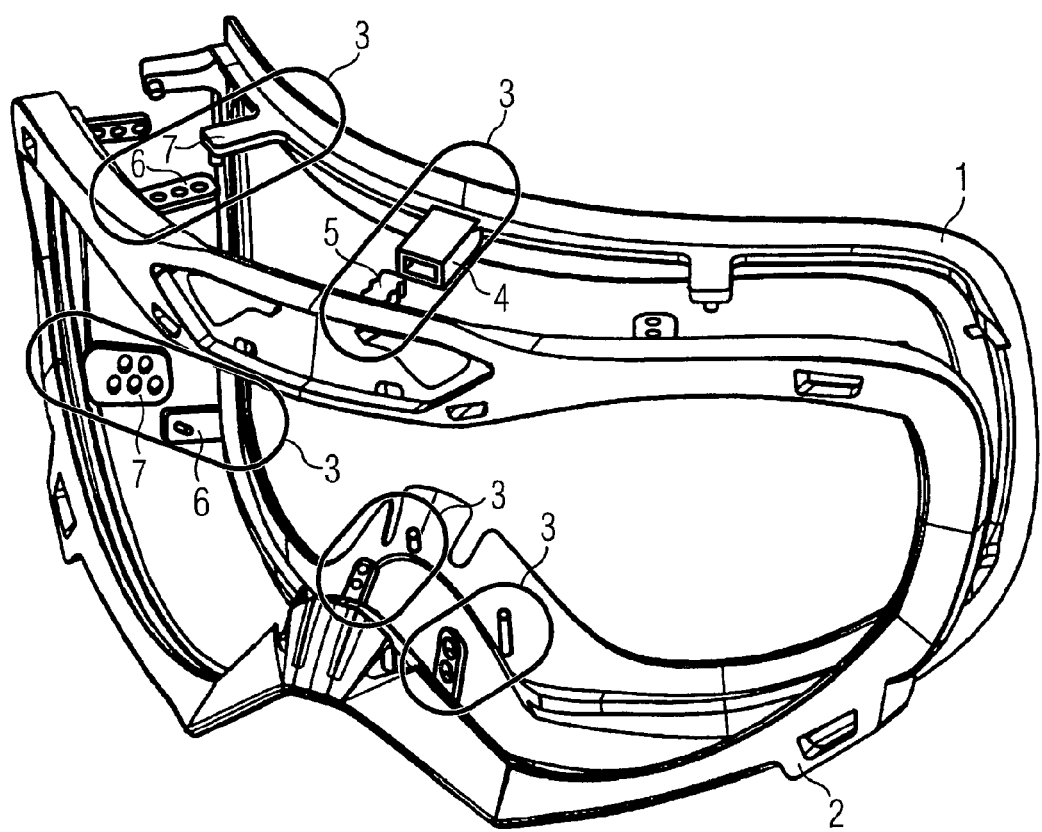
FIG. 1 shows a first embodiment of goggles.

In FIG. 1 a first embodiment of snow sport goggles is illustrated as an example of a face cover device. The goggles comprise a face rest part 1, which is adapted to rest on a user's face. It has a flat surface for ensuring a good and flat contact with the user's face. The face rest part 1 is a molded element made from a flexible material and formed as a closed frame surrounding the eyes of a user, thus resting on the forehead, the cheeks, the nose and the temples of a user upon wear. The goggles further comprise a functional part 2, which comprises a transparent windshield (not illustrated in FIG. 1) which is held by another closed frame. The closed frame of the functional part 2 of the goggles is arranged essentially above the closed frame of the face rest part 1. Around the contour of the closed frames of the functional part 2 and the face rest part 1, a plurality of adjustable connecting sections 3 are arranged, which allow for adjusting the relative position of the face rest part 1 and the functional part 2. As illustrated in FIG. 1, different types of adjustable connecting sections 3 are provided simultaneously on the goggles.

The connecting section 3 arranged on a central upper portion of the goggles comprises a slot 4 as a first part of the connecting section 3, said part being arranged as one piece with the face rest part 1. A slider 5 is arranged as a second part of the connecting section 3 on the closed frame of the functional part 2 and is formed as one piece therewith. Slider 5 and slot 4 are arranged such that they can engage each other in order to form an adjustable connecting section 3. The lateral external surfaces of the slider 5 are undulated, resulting in protrusions. The corresponding internal lateral surfaces of the slot 4 show the corresponding undulation, thus forming recesses which the protrusions on the slider 5 can engage. Correspondingly, a form fit engagement of slider 5 in slot 4 is provided on the adjustable connecting member 3 arranged in the central upper portion of the goggles, allowing for a selection of one of a plurality of predetermined positions of the slider 5 within the slot 4. Slot 4 and slider 5 are each molded parts.

The remaining connecting sections 3 of the first embodiment, which are arranged around the closed frame of the face rest part 1 and the functional part, each comprise a first part 6 having a pin, whereby the first part 6 is arranged as one piece with the closed frame of the face rest part 1. On the closed frame of the functional part 2 a corresponding second part 7 is arranged, being provided with a plurality of holes which the pin of the first part 6 can engage. By selection of one of the plurality of holes in the second part 7, a position of the face rest part 1 relative to the functional part 2 in the area where the adjustable connecting section 3 is arranged can be specifically selected. In the adjustable connecting members 3 shown in the upper part of the goggles according to the first embodiment, the plurality of holes in the second parts 7 are arranged along a straight line. However, when suitable, the plurality of holes can be arranged differently, e.g. such that they cover a certain area, as illustrated in the second part 7 of the adjustable connecting section 3 arranged on the side portion of the goggles. On the nose portion of the goggles, located centrally on the lower part of the goggles, an alternative set-up of an adjustable connecting section 3 is disclosed. Therein the pin is located directly on the closed frame of the face rest part 1. The first 6 and the second 7 parts are molded parts.

The various adjustable connecting sections 3 shown in FIG. 1 are arranged such that the respective first 6 and second 7 parts and the slider 5 and the slot 4 can be completely released, i.e. undone. Correspondingly, the face rest part 1 and the functional part 2 constitute two distinct elements. Therefore, the face rest part 1 can be provided as an exchangeable part. Correspondingly a face rest part 1 suitable for a given shape of the face of a user can be selected and attached to the functional part 2. The different exchangeable face rest parts 1 might differ in the arrangement of the first parts 6 and the slot 4 of the adjustable connecting sections 3 to be formed when engaged with the corresponding second parts 7 and the slider 5 on the functional part 2. In such manner a rough adjustment to a user's face can be accomplished by selection of a face rest part 1, while a fine adjustment is provided by selection of a given position for the various connecting sections 3.

Figure 2:
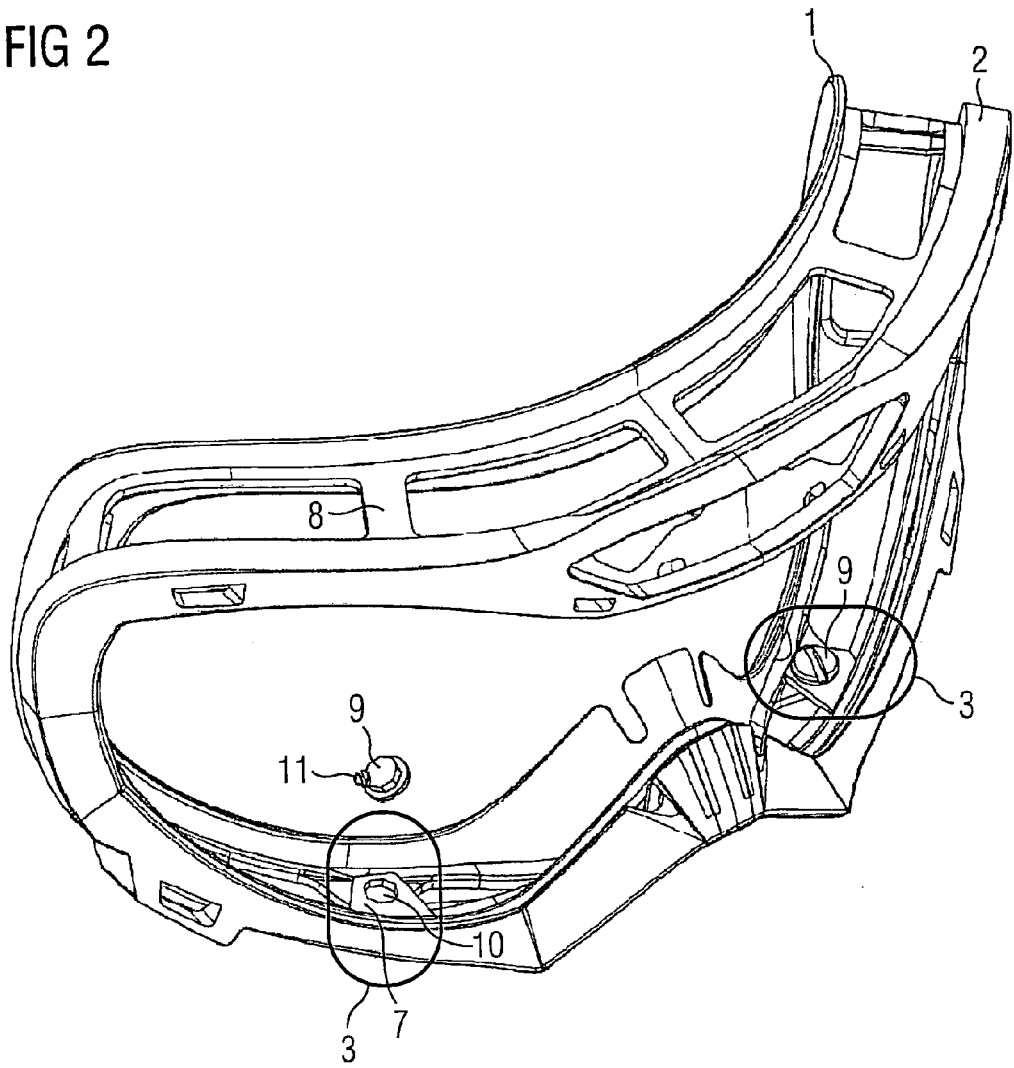
FIGS. 2 and 3 show two views of a second embodiment of goggles.
Figure 3:
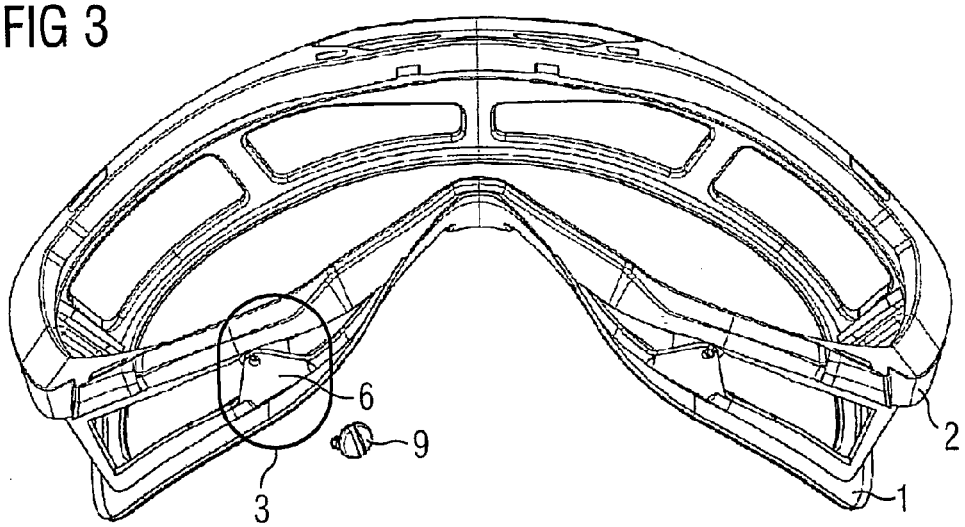

In FIGS. 2 and 3, a second embodiment of the snow sport goggles is illustrated. In FIG. 2 the goggles according to the second embodiment can be seen from above, while they can be seen from below in FIG. 3. In contrast to the first embodiment disclosed in FIG. 1, fixed sections 8 instead of adjustable connecting sections 3 are provided in the upper portion of the goggles in the second embodiment. The face rest part 1 and the closed frame of the functional part 2 are non-adjustably fixed to each other and form a single piece. On the nose part of the goggles, the face rest part 1 and the functional part 2 are likewise non-adjustably fixed to each other.

In the lower part of the goggles, two adjustable connecting sections 3 are provided. These comprise a first part 6 located on the face rest part 1 and a second part 7 located on the closed frame of the functional part 2. The first and the second parts 6, 7 of the adjustable connecting sections 3 can be interconnected by means of a connecting member 9. For this purpose, the connecting member 9 is inserted into a corresponding hole 10 in the second part 7 of the connecting section 3. The connecting member 9 as well as hole 10 have an octahedral shape and the connecting member 9 can be arranged in hole 10 in eight selectably different angular positions. On an opposing face, the connecting member 9 comprises a slot for a screw driver, allowing for easily changing the angular position of the connecting member 9 in the hole 10.

The connecting member 9 is further provided with a pin 11, arranged eccentrically, whereby the pin 11 can be engaged in a corresponding hole in the first part 6 of the connecting section 3. The first part 6 and, thus, the face rest part 1 can be selectively arranged in one of eight positions relative to the second part 7 and, thus, relative to the functional part 2 of the goggles by selection of different angular positions of the connecting member 9 in the hole 10. The various selectable positions of the pin 11 and the face rest part 1 and the functional part 2 relative to each other are located substantially on a circle, thus allowing not only the distance between the face rest part 1 and the functional part 2 to be adjusted, but also the lateral relative position of these parts.

Figure 4:
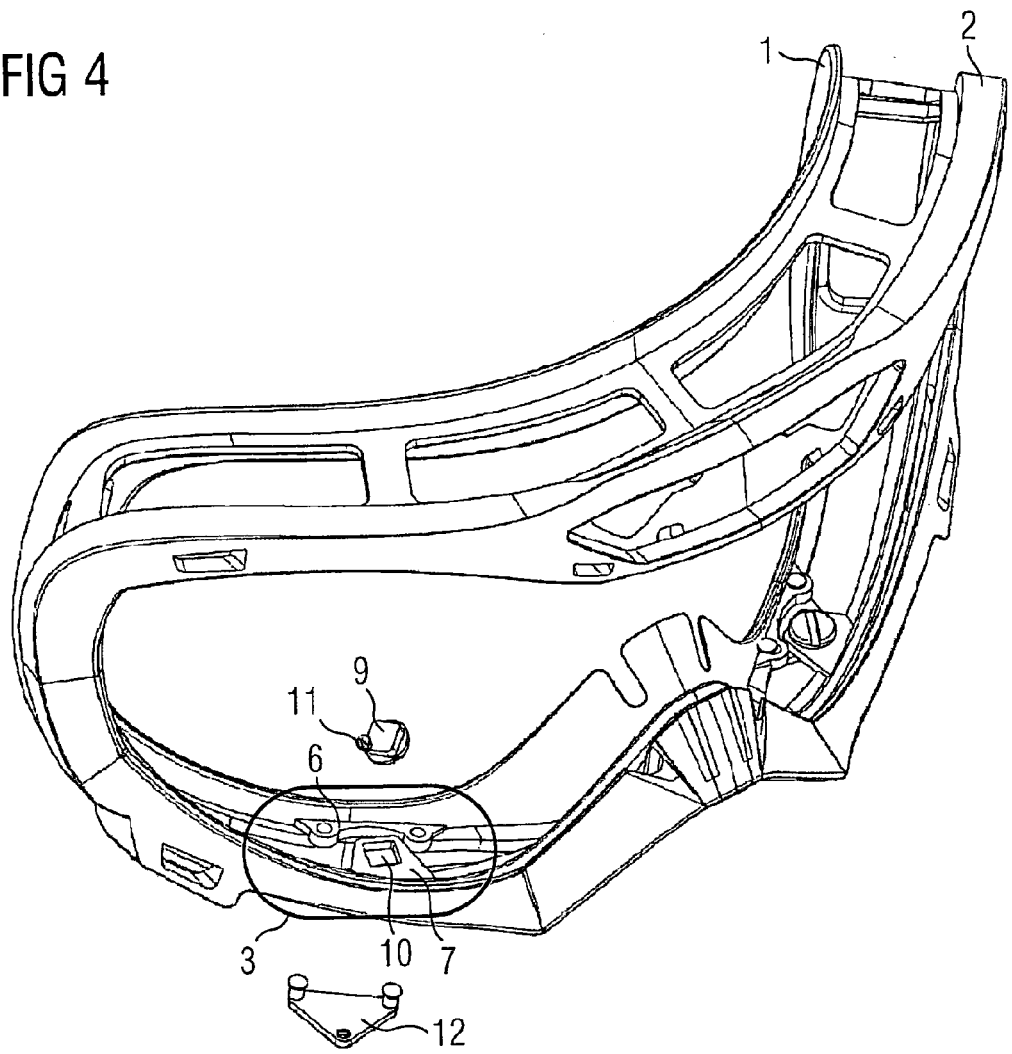
FIG. 4 shows a perspective view of a third embodiment of goggles.

In FIG. 4, a third embodiment of the snow sport goggles is illustrated. It differs from the second embodiment by the set-up of the adjustable connecting sections 3 located on the lower side of the goggles. The second part 7 of the connecting section 3 again comprises a hole 10 into which a connecting member 9 is to be inserted. In contrast to the second embodiment, connecting member 9 and hole 10 both have a square shape in the third embodiment, allowing for selection of four different angular positions of the connecting member 9 in the hole 10. Further, an arranging member 12 is provided having a hole into which pin 11 of the connecting member 9 is to be inserted. The arranging member 12 has pins which allow for an engagement of the arranging member 12 with corresponding holes in the first part of the connecting section 3, which is located on the face rest part 1 of the goggles. Such a set-up simplifies the manufacturing of the goggles and the adjustable connecting section 3 thereof, especially when they are formed by means of a molding process.

Figure 5:
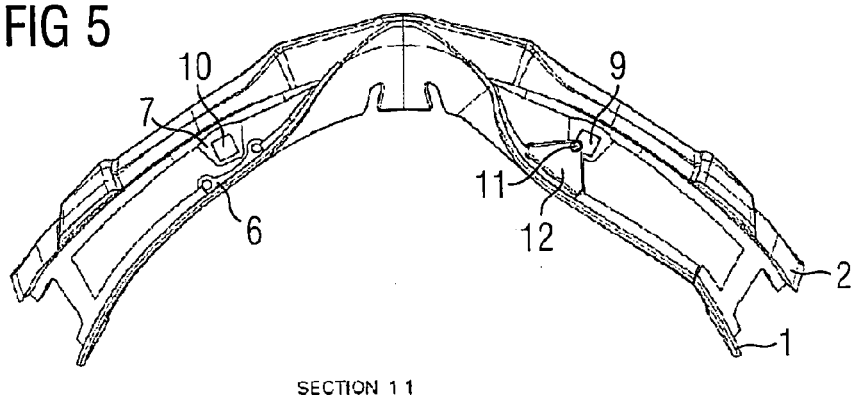
FIGS. 5 to 8 show plan views from above and below of the third embodiment of goggles with different adjustments of the connecting section.
Figure 5:
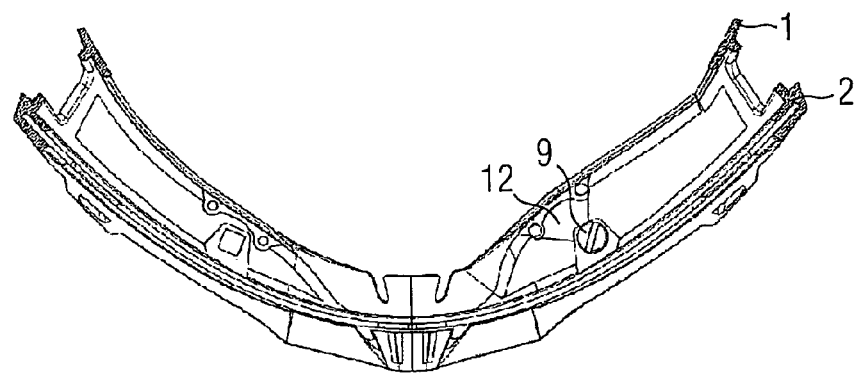

In FIG. 5, plan views from below (upper portion of FIG. 5) and from above (lower portion of FIG. 5) of the third embodiment are illustrated. On the left side of FIG. 5, the connecting member 9 and the arranging member 12 are omitted, while on the right side they are shown. In FIG. 5, the angular position of connecting member 9 in the hole 10 is selected such that the face rest part 1 is shifted towards the nose region of the goggles, while the distance between the face rest part 1 and the functional part 2 is maximized. Such an arrangement is suitable when the user of the goggles has a thin but long nose.

Figure 6:
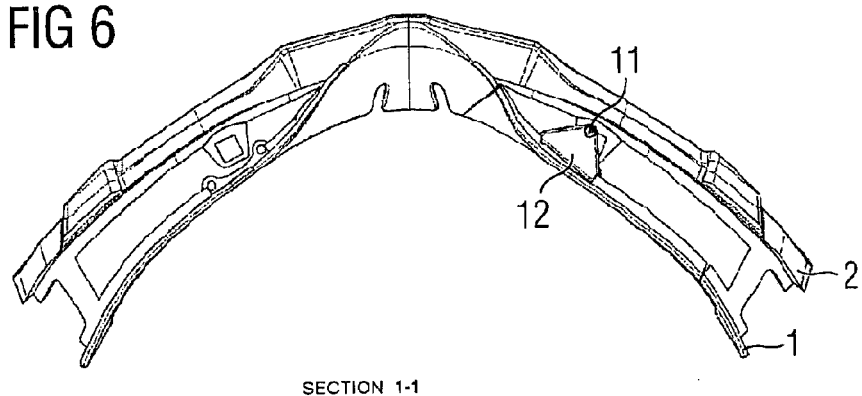
Figure 6:
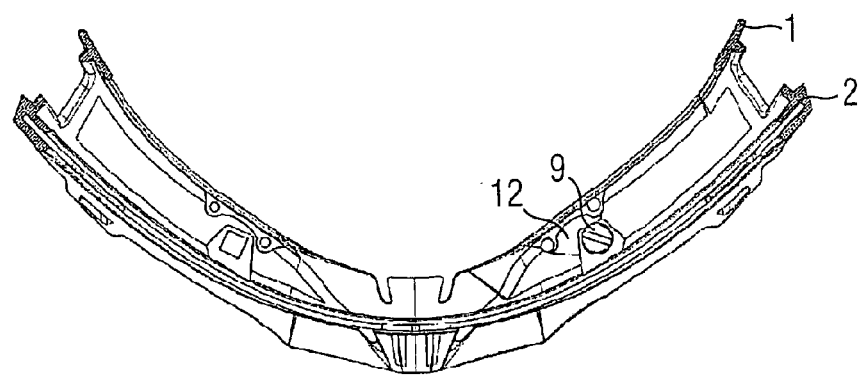

In FIG. 6, the angular position of the connecting member 9 in hole 10 is selected such that the face rest part 1 is shifted towards the nose region of the goggles, while the distance between the face rest part 1 and the functional part 2 is minimized. Such an arrangement is suitable when the user has a thin and short nose.

Figure 7:
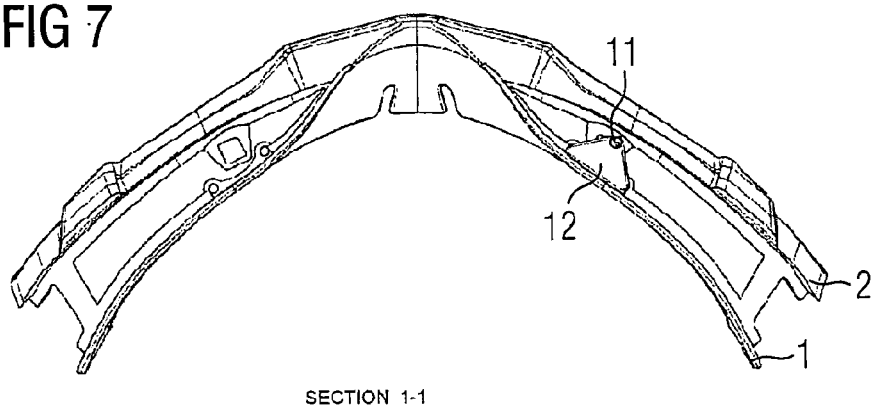
Figure 7:
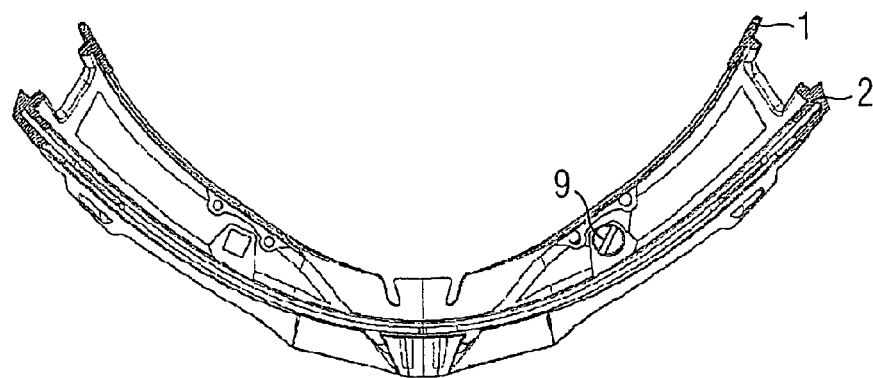

In FIG. 7, the angular position of the connecting member 9 in hole 10 is arranged such that the face rest part 1 is shifted away from the nose region, while the distance between the face rest part 1 and the functional part 2 is minimized. Such an arrangement is suitable when a user has a short but thick nose.

Figure 8:
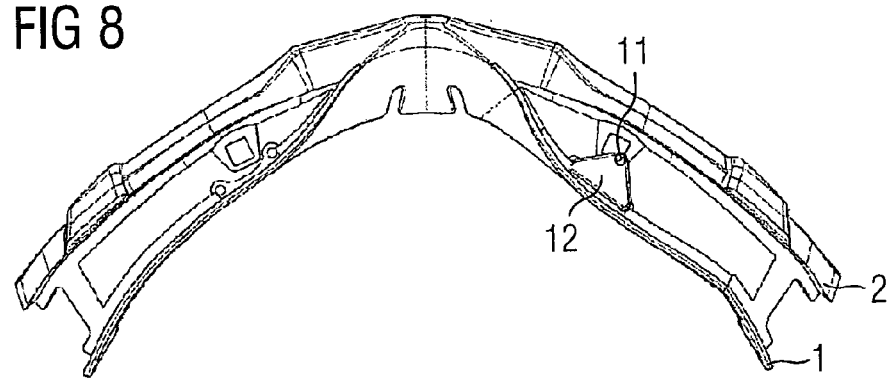
Figure 8:
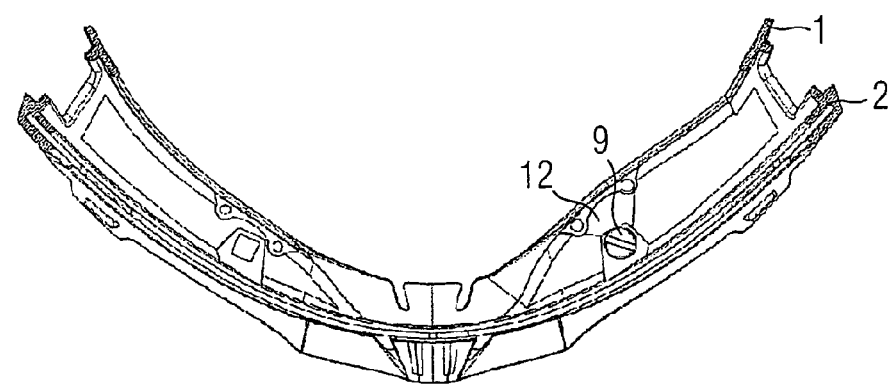

In FIG. 8, the angular position of the connecting member 9 in hole 10 is arranged such that the face rest part 1 is shifted away from the nose region, while the distance between the face rest part and the functional part 2 is maximized. Such an arrangement is suitable when the user has a thick and long nose.

In FIG. 9, a fourth embodiment of the snow sport goggles is illustrated. It differs from the second embodiment by having an additional adjustable connection section 3 located on the upper side of the goggles. This additional adjustable connecting section 3 connects the face rest part 1 and the frame of the functional part 2 and is constituted as an adjustable part. The adjustable part, the face rest part 1 and the frame of the functional part 2 are constituted as a single piece. The adjustable part is made of a flexible material and is provided with a through hole 13, which is arranged such that the shape of the adjustable part of the adjustable connecting section 3 is changed when through hole 13 is deformed. For deformation of the through hole 13 a rigid inserting member 14 is provided. The through hole 13 is circularly shaped in the relaxed state of the adjustable part, i.e. when the through hole 13 it not deformed, e.g. when the inserting member 14 is not inserted therein. The inserting member 14 has a first portion, which is elliptically shaped and adapted to be inserted into the through hole 13, and a second portion, which is adapted for easy manipulation such as adjustment of the angular position of the inserting member 14 when inserted in hole 13. In the illustrated fourth embodiment, the second portion of the inserting member 14 is circular shaped. It might be provided with a slot for a screw driver.

In FIG. 10a a plan view of the adjustable part of the connecting section 3 shown in FIG. 9 with the inserting member 14 inserted into the through hole 13 is illustrated. The adjustable connecting section 3 connects the face rest part 1, located in the upper portion of FIG. 10a, and the functional part 2, located in the lower portion of FIG. 10a. The inserting member 14 is oriented in the through hole 13 such that the long axis of the elliptical first portion points toward the face rest part 1 and the function part 2. This leads to an elliptical deformation of the through hole 13, such that the long axis of the elliptically deformed through hole 13 points equally toward the face rest part 1 and the function part 2. In other words, in comparison with the relaxed state of the adjustable part of the adjustable connecting section 3, the dimension of the adjustable connecting section 3 is increased in the direction of the long axis of the elliptical first portion of the inserting member 14 and consequently the distance between the face rest part 1 and the functional part 2 is equally increased. At the same time the dimension of the adjustable part in the perpendicular direction decreases. As illustrated in FIG. 10a, the deformed through hole 13 does not completely adopt the shape of the elliptically shaped first portion of the inserting member 14.

In FIG. 10b the orientation of the inserting member 14 is changed by 90°. The long axis of the elliptical first portion of the inserting member 14 points in a direction parallel to the face rest part 1 and the functional part 2. This leads to an elliptical deformation of the through hole 13, such that the short axis of the elliptically deformed through hole 13 points toward the face rest part 1 and the function part 2. Thus, the dimension of the adjustable connecting section 3 is decreased in the direction of the short axis of the elliptical first portion of the inserting member 14 and consequently the distance between the face rest part 1 and the functional part 2 is decreased. At the same time the dimension of the adjustable part in the perpendicular direction increases.

In FIGS. 10c and 10d an alternative arrangement of the through hole 13 and the inserting member 14 is illustrated. The through hole 13 adopts a square shape in the relaxed state of the adjustable part, while the inserting member 14 is of rectangular shape, the inserting member 14 having a long and a short side. Upon insertion of the inserting member 14 the through hole 13 completely adopts the shape of the inserting member 14. Similar to the previous arrangement illustrated in FIGS. 10a and 10b, when the long side of the inserting member 14 points in a direction towards the face rest part 1 and the functional part 2, the distance between the face rest part 1 and the functional part 2 is increased (see FIG. 10c), while when the long side of the inserting member 14 points in a direction parallel to the face rest part 1 and the functional part 2, the distance between the face rest part 1 and the functional part 2 is decreased (see FIG. 10d).

The invention claimed is:

1. A face cover device providing a closure over a predetermined area of a face, having a functional part and a face rest part which are interconnected by one connecting section or a plurality of connecting sections, characterized in that the one connecting section or at least one of the plurality of connecting sections is an adjustable connecting section that allows for adjusting the position of the face rest part relative to the functional part by selecting one of a plurality of predetermined positions of the adjustable connecting section, thereby adapting the face rest part to the shape of the face at least in the nose region.

2. The face cover device according to claim 1, characterized in that the adjustable connecting section allows for adjusting the distance between the face rest part and the functional part and/or for adjusting the lateral position of the face rest part relative to the functional part in a direction parallel to a surface of a user's face.

3. The face cover device according to claim 1, characterized by a plurality of adjustable connecting sections that each allow for adjusting the position of the face rest part relative to the functional part independently of each other, wherein preferably each connecting section of the face cover device is an adjustable connecting section.

4. The face cover device according to claim 3, characterized in that the face rest part is comprised of a plurality of sections that are each mechanically independent of each other and are each connected to the functional part by at least one adjustable connecting section.

5. The face cover device according to claim 3, characterized in that the face rest part is flexible, connected to the functional part by a plurality of adjustable connecting sections, and preferably formed as a closed frame.

6. The face cover device according to claim 1, characterized in that the functional part and the face rest part are arranged as a single piece.

7. The face cover device according to claim 1, characterized in that each connecting section is releasable.

8. The face cover device according to claim 1, characterized in that the at least one adjustable connecting section comprises an adjustable part constituted as single piece.

9. The face cover device according to claim 8, characterized in that the adjustable part is deformable in the presence of an external influence, such as heat or an electric or magnetic field, and rigid in the absence of the external influence.

10. The face cover device according to claim 8, characterized in that the adjustable part is flexible and is provided with a hole, further characterized by an inserting member, which can be inserted into the hole, such that the hole deforms in dependence of an angular position of the inserting member within the hole.

11. The face cover device according to claim 1, characterized in that the at least one adjustable connecting section comprises a first part fixed to the face rest part and a second part fixed to the functional part, which can be selectably positioned relative to each other such that the first part and the second part adopt one of a plurality of different positions relative to each other, preferably by means of mechanical, magnetic or electrical forces or by means of a hook and loop fastener stripe.

12. The face cover device according to claim 11, characterized in that one of the first and second parts provides one or several pins and the other one of the first and second parts provides one or several holes which can be selectably engaged by the one or several pins.

13. The face cover device according to claim 11, characterized in that one of the first and second parts comprises a slider and the other one of the first and second parts comprises a slot which the slider can engage at selectably different positions.

14. The face cover device according to claim 11, characterized by a connecting member for connecting the first and second parts, wherein the connecting member can be fixed to the first and the second part in a plurality of selectably different manners.

15. The face cover device according to claim 14, characterized in that the connecting member is insertable at a plurality of selectably different angular positions into a hole arranged in one of the first and second parts, wherein the connecting member comprises at least one pin arranged eccentrically on the connecting member, and the other one of the first and second parts comprises a hole which the pin of the connecting member can engage.

16. The face cover device according to claim 11, characterized by an arranging member for arranging the first and second parts in exactly one position relative to each other, wherein the arranging member is an exchangeable part.

17. The face cover device according to claim 1, characterized by further comprising a deformable closure part extending from the functional part to the skin of a user's face or to the face rest part, which is made of non-breathable material, the closure part preferably being arranged in a deformable shape and/or being constituted of deformable, preferably flexible material.

18. A system comprising a face cover device according to claim 11 and a plurality of arranging members, each of the arranging members allowing for arranging the first and second parts of the face cover device in exactly one position relative to each other, wherein a first and a second arranging member of the plurality of arranging members allow for a first and a second position of the first and second parts relative to each other, the first and second positions being different from each other.

19. A system comprising a face cover device according to claim 7 and at least one further face rest part adapted for being attached to the functional part of the face cover device and for replacing the first face rest part of the face cover device, wherein the first face rest part of the face cover device and the further face rest part are adapted for different shapes of a face.

20. The face cover device according to claim 8, characterized in that the shape of the adjustable part is adjustable.

21. The face cover device according to claim 1, characterized in that the adjustable connecting section is constituted as a single piece.

22. The face cover device according to claim 8, characterized in that the hole is a through hole.

23. The face cover device according to claim 8, characterized in that the length of the adjustable part is adjustable.

* * * * *